United States Patent
Duquette et al.

(10) Patent No.: US 10,156,232 B2
(45) Date of Patent: *Dec. 18, 2018

(54) HIGH FREQUENCY OSCILLATOR VENTILATOR

(71) Applicant: CareFusion 207, Inc., San Diego, CA (US)

(72) Inventors: Steven Duquette, Laguna Niguel, CA (US); Thomas Westfall, Riverside, CA (US); Steve Han, Garden Grove, CA (US)

(73) Assignee: CareFusion 207, Inc., San Diego, CA (US)

( * ) Notice: Subject to any disclaimer, the term of this patent is extended or adjusted under 35 U.S.C. 154(b) by 320 days.

This patent is subject to a terminal disclaimer.

(21) Appl. No.: 15/231,671

(22) Filed: Aug. 8, 2016

(65) Prior Publication Data

US 2016/0348665 A1    Dec. 1, 2016

Related U.S. Application Data

(63) Continuation of application No. 11/269,488, filed on Nov. 8, 2005, now Pat. No. 9,427,540.

(51) Int. Cl.
*F04B 45/047* (2006.01)
*F04B 49/06* (2006.01)
(Continued)

(52) U.S. Cl.
CPC ....... *F04B 45/047* (2013.01); *A61M 16/0009* (2014.02); *A61M 16/0057* (2013.01);
(Continued)

(58) Field of Classification Search
CPC .......... A61M 16/0096; A61M 2205/42; A61M 2016/0027; A61M 2205/0288
See application file for complete search history.

(56) References Cited

U.S. PATENT DOCUMENTS 3,201,529 A    8/1965 Surh
4,719,910 A    1/1988 Jensen
(Continued)

FOREIGN PATENT DOCUMENTS

EP    1106197 A2    6/2001

OTHER PUBLICATIONS

Chinese Notice of Reexamination for Application No. 200680045540.5, dated Dec. 8, 2015, 4 pages excluding translation.

*Primary Examiner* — Kristen Matter
(74) *Attorney, Agent, or Firm* — Morgan, Lewis & Bockius LLP

(57) ABSTRACT

Provided is a high frequency oscillating ventilator comprising a housing assembly, a linear actuator, a linear coil, a piston mounted on a pushrod, a diaphragm dividing a housing into a first and second side and having an opening formed on the second side that is fluidly connected to the patient's airway for delivering gas thereto. The linear actuator is fixedly mounted to the housing assembly and has a linear coil coaxially disposed therewithin. A pushrod supports the linear coil on the linear actuator to allow relative axially sliding therebetween. The piston is directly mounted to the diaphragm such that reciprocation thereof as effectuated by the linear coil cooperating with the linear actuator alternately produces positive and negative pressure waves in the gas in the patient's airway.

20 Claims, 4 Drawing Sheets

(51) Int. Cl.
*F04B 45/04* (2006.01)
*A61M 16/00* (2006.01)
*A61M 16/04* (2006.01)
*A61M 16/08* (2006.01)
*A61M 16/20* (2006.01)

(52) U.S. Cl.
CPC ........ *A61M 16/0096* (2013.01); *A61M 16/04* (2013.01); *A61M 16/0875* (2013.01); *A61M 16/208* (2013.01); *F04B 45/041* (2013.01); *F04B 49/06* (2013.01); *A61M 2016/0027* (2013.01); *A61M 2205/0288* (2013.01); *A61M 2205/42* (2013.01)

(56) References Cited

U.S. PATENT DOCUMENTS

| | | | |
|---|---|---|---|
| 4,747,402 A | 5/1988 | Reese et al. | |
| 4,805,612 A | 2/1989 | Jensen | |
| 4,821,709 A | 4/1989 | Jensen | |
| 5,107,830 A | 4/1992 | Younes | |
| 5,165,398 A | 11/1992 | Bird | |
| 5,307,794 A | 5/1994 | Rauterkus et al. | |
| 5,345,206 A | 9/1994 | Morcos | |
| 5,555,880 A | 9/1996 | Winter et al. | |
| 5,632,269 A | 5/1997 | Zdrojkowski | |
| 5,692,497 A | 12/1997 | Schnitzer et al. | |
| 5,755,223 A | 5/1998 | Schaible et al. | |
| 6,085,746 A | 7/2000 | Fox | |
| 6,158,433 A | 12/2000 | Ong et al. | |
| 6,390,092 B1 | 5/2002 | Leenhoven | |
| 6,694,978 B1 | 2/2004 | Bennarsten | |
| 7,164,336 B2 | 1/2007 | Rausch et al. | |
| 9,427,540 B2 * | 8/2016 | Duquette | A61M 16/0096 |
| 2003/0200970 A1 | 10/2003 | Stenzler et al. | |
| 2005/0212363 A1 | 9/2005 | Okubo | |

* cited by examiner

HIGH FREQUENCY OSCILLATOR VENTILATOR

CROSS-REFERENCE TO RELATED APPLICATIONS

The present application claims the benefit of priority under 35 U.S.C. § 120 as a continuation of U.S. patent application Ser. No. 11/269,488 entitled "High Frequency Oscillator Ventilator," filed on Nov. 8, 2005, the disclosure of which is hereby incorporated by reference in its entirety for all purposes.

STATEMENT RE: FEDERALLY SPONSORED RESEARCH/DEVELOPMENT (Not applicable)

BACKGROUND OF THE INVENTION

The present invention relates generally to medical equipment and, more particularly, to a high frequency oscillating ventilator for producing positive and negative pressure waves in respiratory air that is supplied to a patient. Advantageously, the high frequency oscillating ventilator (HFOV) of the present invention is specifically configured to operate at reduced noise levels and under reduced power as compared to HFOV's of the prior art.

As opposed to conventional ventilators which ventilate only during the inhalation phase and which rely on human physiological response for ventilation during the expiration phase, HFOV's produce an active exhalation which is critical in the respiration of certain types of patients such as in neonates and/or other child or adult patients suffering from certain lung diseases. In some cases, the lungs of the patient may be incapable of providing adequate ventilation or gas exchange, particularly in the exhalation phase.

In this regard, HFOV's are specifically developed to provide sufficient gas exchange and full oxygenation of a patient whose respiratory abilities in the exhalation phase are compromised. Despite their advantages, HFOV's of the prior art suffer from several deficiencies that detract from their overall utility. For example, one of the more popular HFOV's is constructed similar to that shown and described in U.S. Pat. No. 4,719,910 issued to Jensen and entitled OSCILLATING VENTILATOR AND METHOD (the "Jensen reference"), the entire contents of which is expressly incorporated by reference herein.

The HFOV of the Jensen reference comprises a housing having a magnet and a diaphragm disposed therewithin. A coil is mounted on the first side of the diaphragm and is operative to reciprocate a piston on the first side. The HFOV includes the appropriate circuitry to reverse current polarity in the coil in order to effectuate reciprocation of the piston which, in turn, causes the diaphragm to move back and forth within the housing. The vibrating diaphragm creates positive and negative pressure waves in gas which is supplied to the patient's airway.

Although the HFOV as disclosed in the Jensen reference is effective in producing gas exchange in ventilation of a patient without damaging the patients lungs such by overpressurization, this HFOV unfortunately produces relatively high noise levels which are undesirable in sensitive environments wherein HFOV's are typically used such as neonatal intensive care units. Furthermore, the HFOV of the Jensen reference relies on an arrangement of spider springs to suspend a linear actuator portion of the coil. Unfortunately, a relatively large amount of power is required to overcome the significant spring forces when reciprocating the linear actuator relative to the coil to cause the diaphragm to vibrate.

Furthermore, the above-described HFOV relies on a dedicated source of gas to cool the coil as well as provide respiratory gasses for the patient. In addition, a fan may be incorporated into the HFOV in order to create sufficient flow of the cooling gasses through the coil. In this regard, a further deficiency associated with this HFOV is excess heating of the coil which degrades the accuracy with which the piston is centered due to resistance changes in the coil as the coil heats up.

High noise levels produced by prior art HFOV's noise may be generated by several sources including noise produced by the fan as well as noise produced by the flow of cooling air traveling through various passageways formed in the coil. Because such cooling gas exit the coil and enter the surrounding environment, additional noise is produced by the out rush of cooling gas through apertures in the coil housing.

A further significant source of noise that may be disruptive to patients as well as to hospital personnel is noise that is generated by the diaphragm. More specifically, in the prior art HFOV described above, the diaphragm includes a relief provided around a circumferential peripheral edge thereof. The relief allows the piston to reciprocate in unison with the diaphragm in order to produce the positive and negative pressure waves in the patient airway. Unfortunately, the consistent back and forth motion of the diaphragm causes the relief to constantly invert in rapid succession creating a snapping noise as the reciprocations occur.

A further source of noise is generated by the piston as it contactor strikes an underside the diaphragm in a repetitive manner during each positive stroke. The constant repetitive striking of the bottom of the diaphragm generates the repetitive slapping noise which only adds to the overall noise produces by the HFOV and which unfortunately disrupts the patient's sleep and recovery. For example, HFOV's of the type described above may produce noise levels of up to 65 dB when operating at full power.

As can be seen, there exists a need in the art for an HFOV that is specifically configured to operate effectively but with reduced sound output in order to avoid disturbing the sleep and rest of patients dependent thereupon. Furthermore, there exists a need in the art for an HFOV that operates at reduced power and which is more energy-efficient than current HFOV's but which matches the clinical performance of existing HFOV's. Additionally, there exists a need in the art for an HFOV that is of reduced size for increased portability in order that the HFOV may be utilized while transporting critically ill patients. Finally, there exists a need in the art for an HFOV that is of simple construction and low cost.

BRIEF SUMMARY OF THE INVENTION

The present invention specifically addresses and alleviates of the above-referenced deficiencies associated with high frequency oscillating ventilators (HFOV's) of the prior art. More particularly, the present invention is an improved HFOV that is configured to match the clinical performance of existing HFOV's but at a reduced size and with reduced noise and power consumption through the use of a pushrod-suspended linear coil as well as the incorporation of a rolling diaphragm in the HFOV and which is directly engaged to a piston.

The HFOV of the present invention includes a housing assembly having a linear actuator fixedly mounted thereto. A linear coil is coaxially disposed within the linear actuator and is suspended thereon by a pushrod which extends axially through the linear actuator in a manner to allow axial reciprocation of the linear coil. The piston is mounted on one end of the pushrod with the linear coil being mounted on an opposite end of the pushrod. The diaphragm sealingly divides the housing assembly into a first side and a second side. The diaphragm is operatively engaged to the piston and is preferably configured to be removable and/or replaceable such that the HFOV may be transferred between patients.

Replaceability of the diaphragm is facilitated through the use of a cone cover which is secured to a housing assembly of the HFOV by a pair of hold down brackets. A pair of thumbscrews secured into the housing assembly through opposing ends of the hold down brackets allow for quick release and removal of the cone cover for access to the diaphragm. An opening formed in the cone cover fluidly communicates with the patient's airway for delivering gas thereto. The gas is supplied by a source of gas such as compressed gas or oxygen.

As is shown and disclosed in U.S. Pat. No. 5,345,206 issued to Morcos and entitled MOVING COIL ACTUATOR UTILIZING FLUX-FOCUSED INTERLEAVED MAGNETIC CIRCUIT, the entire contents of which is expressly incorporated by reference herein, the actuator assembly may be configured as a voice coil similar to that which is commercially available from BEI Electronics, Inc. of San Marcos, Calif., wherein the linear coil and linear actuator of the voice coil cooperate to effectuate reciprocation of the diaphragm in such a manner to alternately produce positive and negative pressure waves in the gas in the patient's airway.

Noise produced by the HFOV of the present invention is greatly reduced compared to conventional HFOV's due to the incorporation of a deep radius groove formed about a periphery of the diaphragm such that the diaphragm is essentially non-inverting. The specific configuration of the diaphragm of the present invention eliminates a popping sound that occurs during rapid frequency oscillations of the piston and diaphragm in prior art HFOV's. Furthermore, the diaphragm of the present invention is directly affixed or attached to the piston as opposed to an intermittent engagement that occurs therebetween during the forward stroke of the piston of prior art HFOV's. Such direct attachment of the piston to the diaphragm eliminates the slapping sound that is generated by prior art HFOV's when the piston repetitively strikes the underside of the diaphragm during the piston's forward stroke.

As was earlier mentioned, power consumption of the HFOV of the present invention is also reduced as compared to prior art HFOV's due to the use of a pushrod extending through the linear actuator which results in an essentially free-floating linear coil. As compared to prior art HFOV's which use radially-extending spider springs for centering and maintaining the position of the linear coil and piston, power consumption in the HFOV of the present invention is greatly reduced due to the lack of spring forces.

Advantageously, the centering of the piston in the present invention is facilitated by a sensor such as an optical sensor which is connected to the pushrod. An inner-loop control system provides a closed-loop feedback mechanism by which the position of the piston is accurately maintained at all times despite variations in temperature in the coil which, as was earlier mentioned, affects the accuracy with which the piston is centered. Cooling of the actuator assembly of the present invention is facilitated through the use of ventilation ports formed in the housing assembly which allow for convective cooling by atmospheric air circulating through the actuator assembly.

BRIEF DESCRIPTION OF THE DRAWINGS

These as well as other features of the present invention will become more apparent upon reference to the drawings wherein.

DETAILED DESCRIPTION OF THE INVENTION

Figure 1:
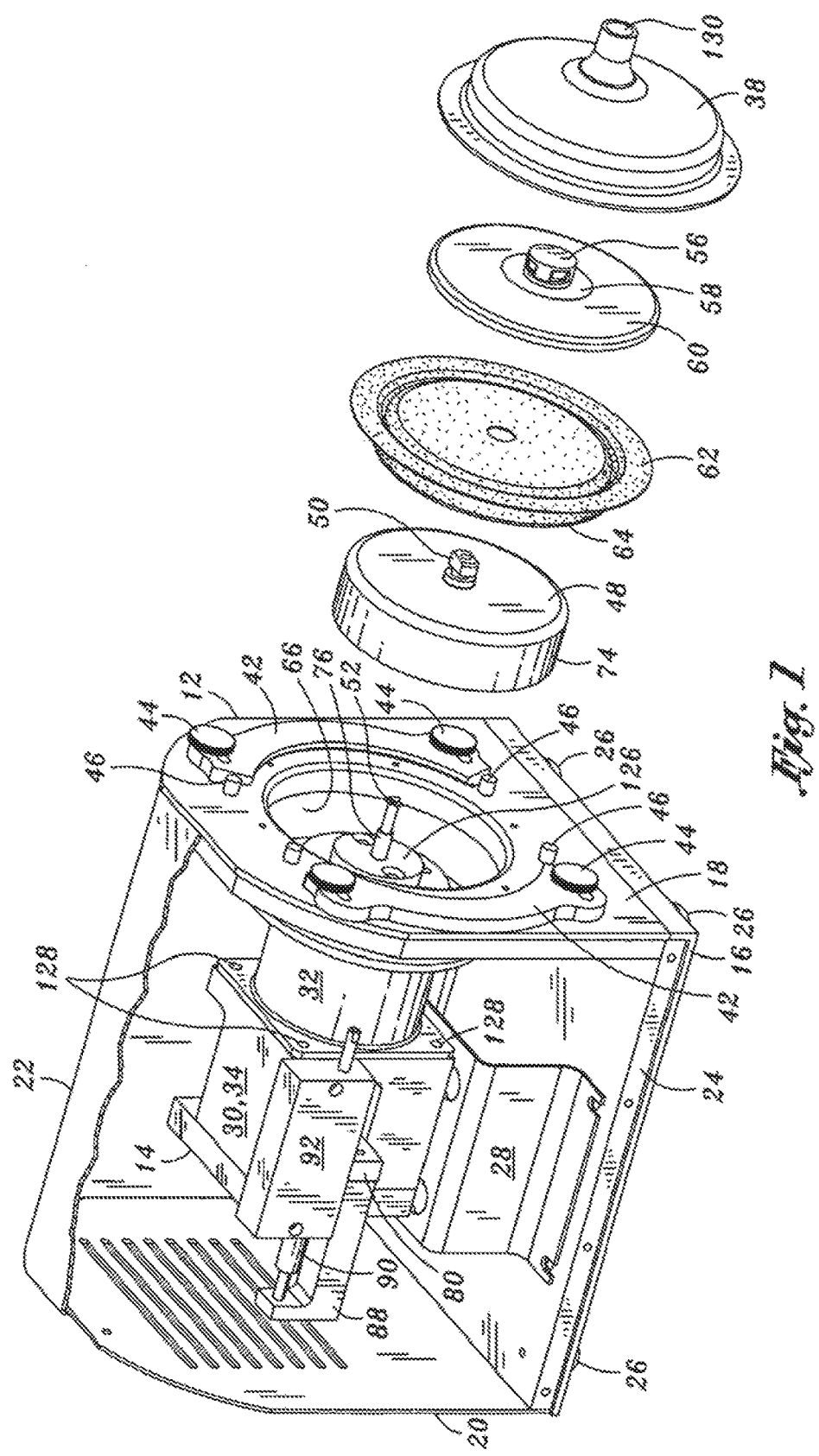
FIG. 1 is a perspective partial sectional view of a frequency oscillating ventilator (HFOV) of the present invention.
Figure 2:
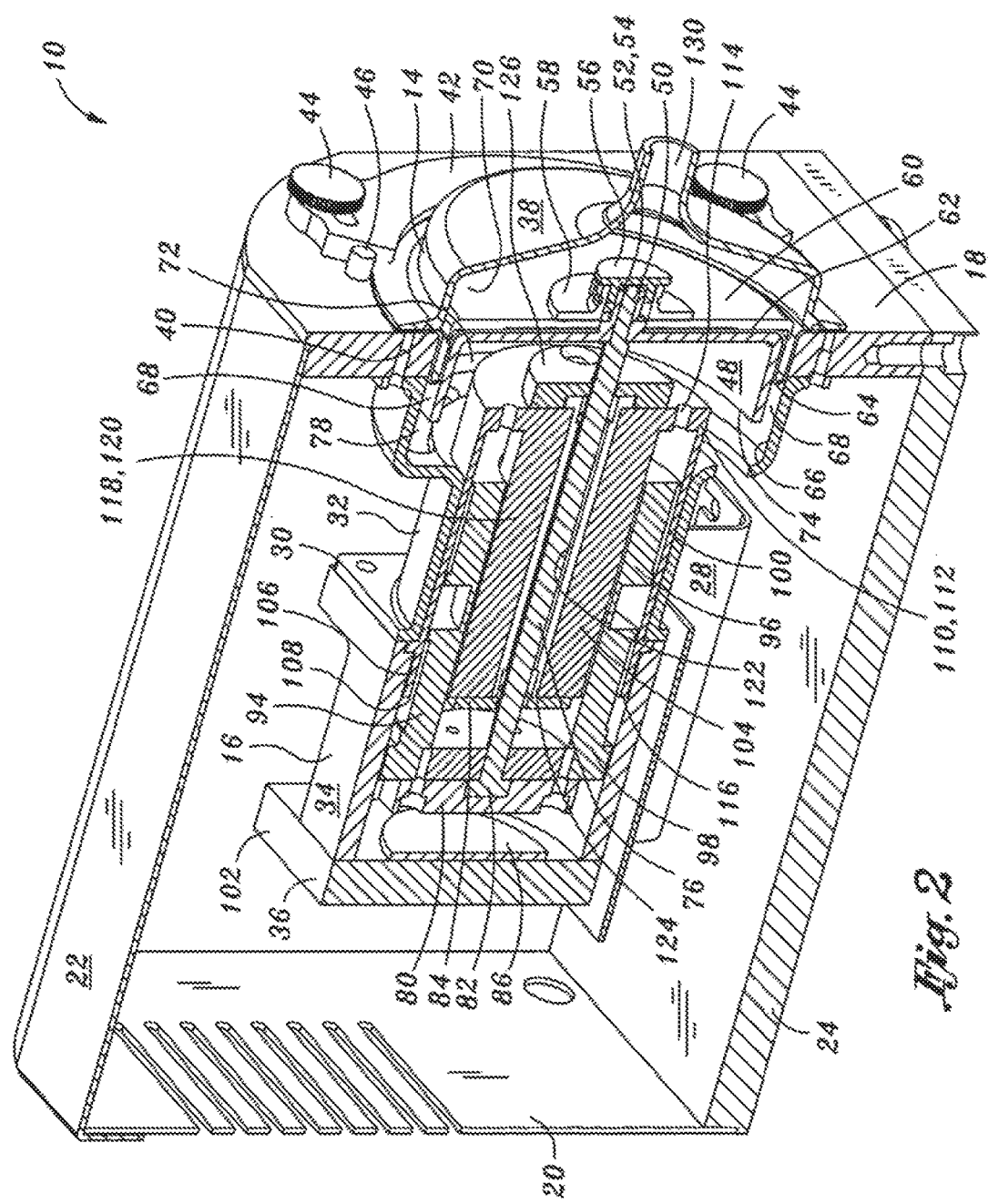
FIG. 2 is a partially exploded perspective view of the HFOV of the present invention illustrating a removable diaphragm having a non-inverting deep radius groove which is directly attached to a piston reciprocating within the HFOV.
Figure 3:
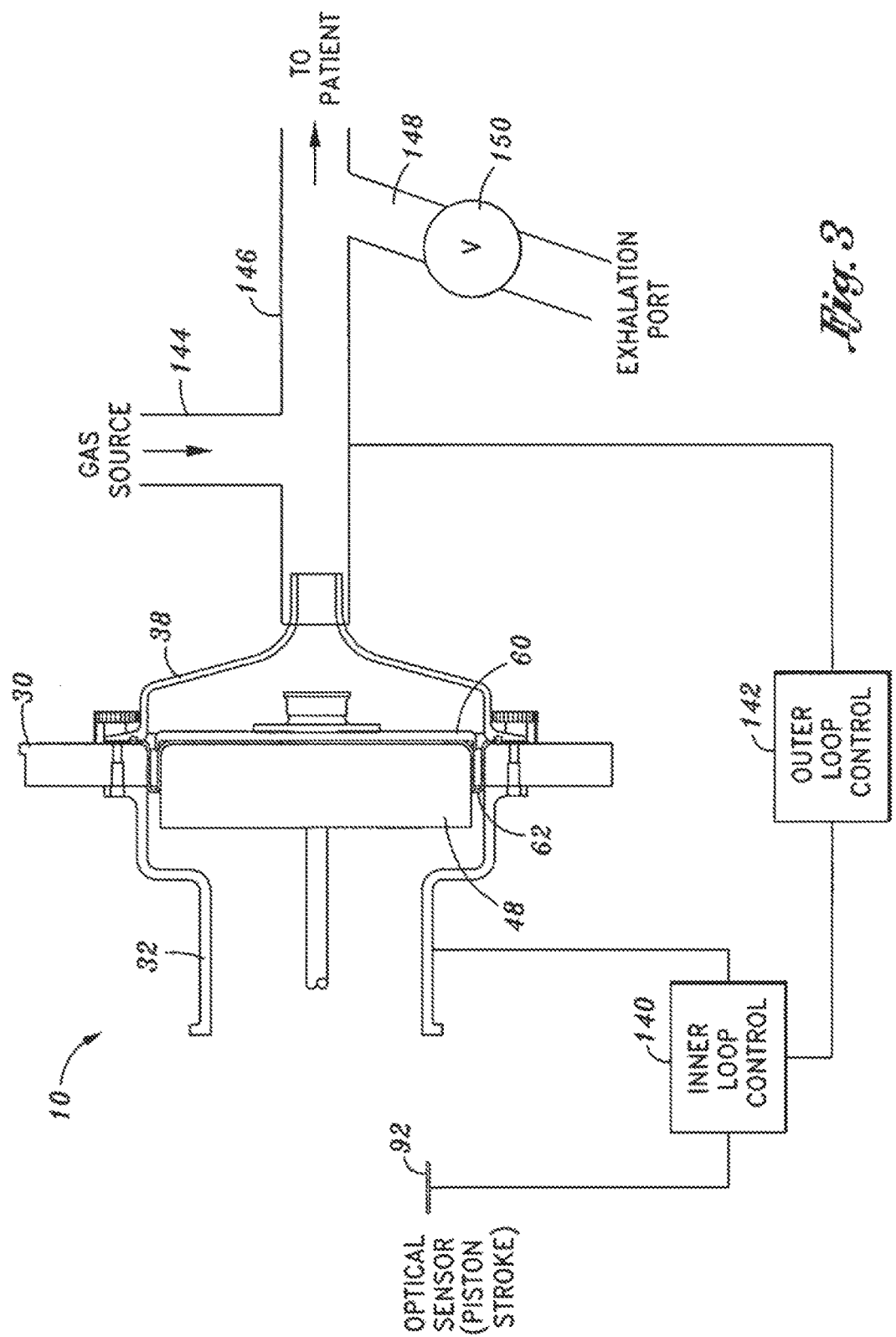
FIG. 3 is a schematic diagram of the HFOV of the present invention as incorporated into a ventilating system and further illustrating an inner and outer control loop for regulating the operation thereof.

The present invention will now be described in particular with reference to the accompanying drawings wherein FIGS. 1-3 illustrate a high frequency oscillating ventilator (HFOV) 10 which, in its broadest sense, comprises a housing assembly 30 having an actuator assembly 102 mounted thereupon. The actuator assembly 102 is comprised of a linear actuator 104 and a linear coil 94 having a pushrod 76 which supports the linear coil 94 on the linear actuator 104. The pushrod 76 is axially slideable within the linear actuator 104 and is directly mounted to a diaphragm 62 which sealingly divides the housing assembly 30 into a first side 70 and a second side 72. The actuator assembly 102 is configured to effectuate reciprocation of the piston 48 and diaphragm 62 in a manner to alternately produce positive and negative pressure waves in gas provided to a patient's airway.

Figure 2A:
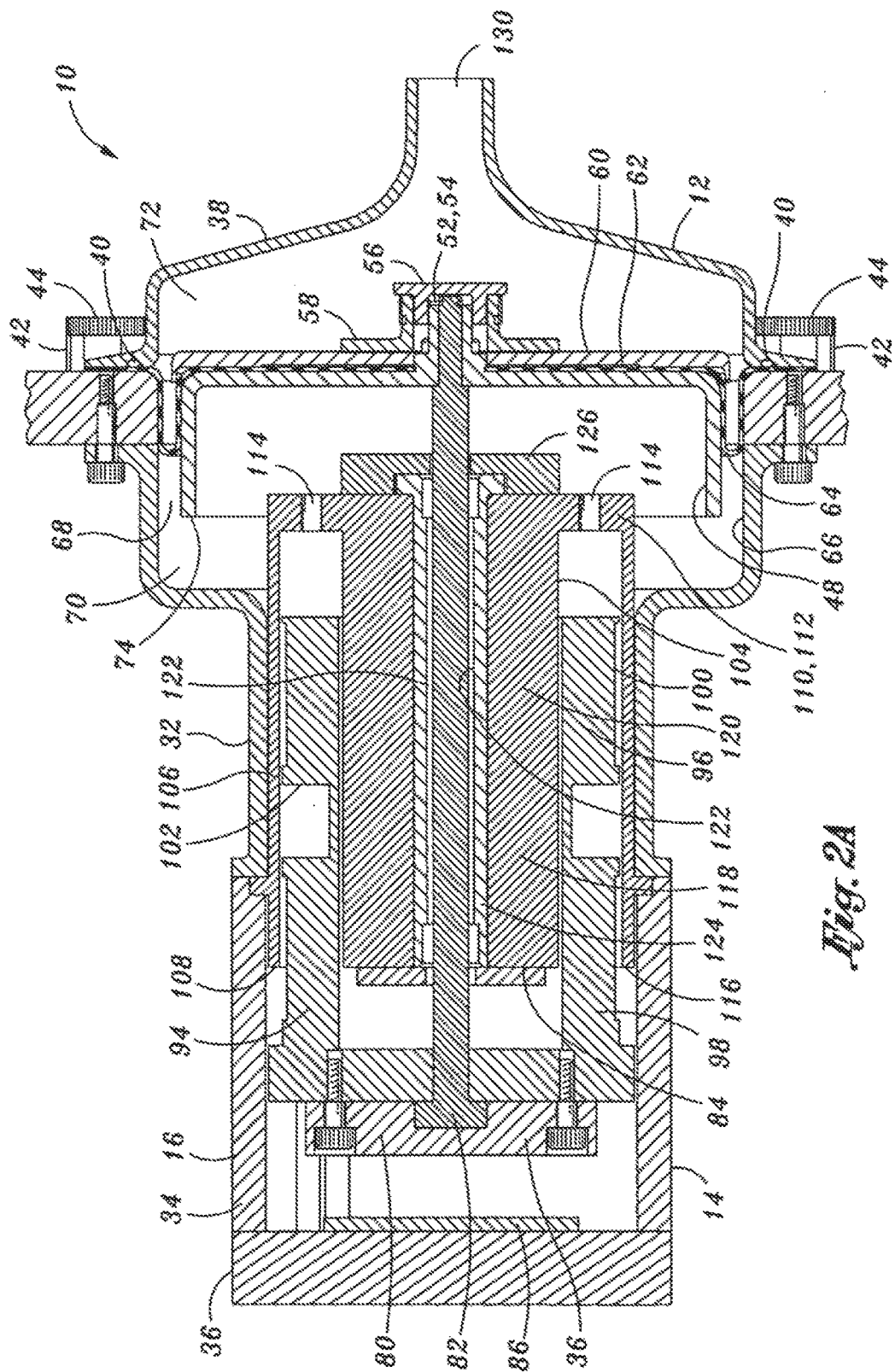
FIG. 2A is a cross-sectional side view of an actuator assembly having a linear coil and linear actuator and illustrating the linear coil being reciprocatively mounted via a push rod sliding axially within the linear actuator.

The actuator assembly 102 may be configured as a linear motor which is similar to the type shown and described in U.S. Pat. No. 5,345,206 issued to Morcos and entitled MOVING COIL ACTUATOR UTILIZING FLUX-FOCUSED INTERLEAVED MAGNETIC CIRCUIT, the entire contents of which is expressly incorporated by reference herein (the Morcos reference). As can be seen in FIGS. 2 and 2A, the actuator assembly 102 is comprised of the linear actuator 104 that it mounted within the housing assembly 30. The linear coil 94 can be seen in the figures as being coaxially disposed within the linear actuator 104. The actuator assembly 102 of the type disclosed in the Morcos reference may also be referred to as a voice coil and is commercially available from BEI Electronics, Inc. of San Marcos, Calif. Preferably, the HFOV 10 of the present invention utilizes BEI Electronics voice coil Model No. LA25 although alternative embodiments may be utilized in the present invention.

Importantly, the unique configuration of the diaphragm 62 of the present invention achieves a reduced noise level as compared to noise produced by prior art HFOV's 10 due to the incorporation of a deep radius groove 64 formed about a periphery of the diaphragm 62. Because of its depth, the groove 64 is non-inverting during reciprocation of the piston 48 which eliminates a popping noise that is commonly produced by diaphragms 62 that have a relatively shallow relief rather than a deep radius groove 64. In prior art HFOV's 10, the relief in the diaphragm 62 is continuously inverting during oscillation of the piston 48 which results in the loud popping sound.

As was earlier mentioned, the piston or plate member 48 of the present invention may be directly attached to the diaphragm 62 as is shown in the figures. Advantageously, such direct attachment between the piston 48 and the diaphragm 62 eliminates a slapping noise that occurs in HFOV's 10 of the prior art when the piston 48 strikes the diaphragm 62 on its positive stroke. However, in the present invention, the diaphragm 62 may be captured between the piston 48 and a cover plate 60 disposed on the second side 72 of the housing assembly 30. The diaphragm 62 is interposed between the cover plate 60 and the piston 48. The diaphragm 62 and deep radius groove 64 generally conform to the piston 48 shape and, in this regard, the piston 48, diaphragm 62 and cover plate 60 are generally disk-shaped although other shapes may be utilized. The piston 48 has a piston flange 74 which extends about a peripheral edge thereof. The piston flange 74 preferably has a depth that is generally greater than the depth of the deep radius groove 64 as shown in the figures.

The housing assembly 30 may be separated into a forward housing 32 and an aft housing 34 with the forward housing 32 defining a cylinder bore 66 within which the piston 48 may reciprocate. The cylinder bore 66 and piston flange 74 are generally separated by an annular gap 68 that is preferably sized and configured to be complementary to the groove 64 of the diaphragm 62. More particularly, a spacing of the annular gap 68 is preferably generally equivalent to that of a thickness or width of the groove 64. In this manner, reciprocation of the piston 48 results in a rolling motion of the groove 64 during forward and aft strokes. During the forward stroke of the piston 48, the groove 64 of the diaphragm 62 is gradually drawn away from the cylinder bore 66 as the piston 48 moves in a forward direction.

Conversely, as the piston 48 direction reverses and the piston 48 moves in the aft direction, the groove 64 rolls back against the cylinder bore 66 and, once the piston 48 passes the neutral point, the groove 64 in turn is drawn away from the piston flange 74. In this manner, a rolling motion of the groove 64 is produced which results in virtually zero noise being produced due to movement of the reciprocation of the diaphragm 62. It can be seen that depending on the stroke of the piston 48, the groove 64 is preferably sized to avoid inversion of the groove 64 as is common in the generally noisier HFOV's 10 of the prior art.

Referring to FIGS. 1-2A, the cover plate 60 is shown as preferably having a lip formed about a peripheral edge thereof. The lip is formed complementary to the piston flange 74 such that the diaphragm 62 is essentially captured in a manner that limits flexing of the diaphragm 62 to the deep radius groove 64 portion. Radially beyond the groove 64, the diaphragm 62 has a peripheral edge which extends about a circumference thereof and which is captured between a mounting bracket 16 and a cone cover 38 of the HFOV 10. The cone cover 38 may include an annular groove extending thereabout which is configured to receive an 0-ring 40. The 0-ring 40 may be provided to seal the second side 72 that is fluidly connected to the patient and which is collectively defined by the cone cover 38 and the cone cover 38 includes an opening 130 which is connectable to a patient tube 146 that provides gas to the patient airway. Shown as being generally conically shaped, the cone cover 38 is preferably sized complementary to the stroke of the piston 48 such that the pressure waves that are produced thereby may be directed through the opening 130 and into the patient tube 146.

Although the cone cover 38 may be permanently mounted to the mounting bracket 16, such mounting arrangement would reduce the ability to remove and replace certain components of the HFOV 10 that come into contact with fluids emanating from the patient. In this regard, the cone cover 38 is preferably mounted on the mounting bracket 16 such that the diaphragm 62, which comes into contact with fluid from the patient, is easily removable such that it may be disinfected and reused and/or entirely replaced prior to transferring the HFOV 10 from one patient to the next. Removal of the cone cover 38 to allow access to the diaphragm 62 is facilitated through the use of the hold down brackets 42 being secured to the mounting bracket 16 via a pair of thumbscrews 44. The hold down bracket 42 may have a generally semi-circular shape formed complementary to the cone cover 38 such that each one of the hold down brackets 42 engages a portion of the lip of the cone cover 38.

The mounting bracket 16 may include a pair of posts or stops 46 extending outwardly and against which opposing ends of the hold down brackets 42 may bear in order to position the hold down bracket 42 in proper registry with the cone cover 38 for even clamping thereof. Advantageously, the thumbscrews 44 provide a quick release mechanism by which the cone cover 38 is secured to the housing bracket. As can be seen in FIG. 1, a pair of the hold down brackets 42 are disposed on opposing sides of the mounting bracket 16 although any number of hold down brackets 42 may be used and may be provided in any configuration and size.

The pushrod 76 can be seen extending through the piston 48, diaphragm 62 and cover plate 60 to terminate at a free end of the pushrod 76. A shoulder may be included on an end of the pushrod 76 against which the piston 48 may be seated. A pair of diametrically opposed flats 50 may be provided on the free end of the pushrod 76. Apertures 114 formed in the piston 48, diaphragm 62 and cover plate 60 are preferably configured to be complementary to the flats 50 in order to prevent rotation thereof during reciprocation of the piston 48. As may he appreciated, rotation of the diaphragm 62 would otherwise cause undue twisting of the deep radius groove 64 of the diaphragm 62 which could compromise the structural integrity thereof.

A plate cap 58 may he secured over the cover plate 60 and may be held on the push rod by an E-ring 52 inserted into a circumferential pushrod groove 54 formed on the extreme end of the pushrod 76. Preferably, the E-ring 52 is configured to prevent axial movement of the piston 48 relative to the pushrod 76. The piston 48 may further include a collar extending upwardly therefrom to the E-ring 52. A cap cover 56 may be inserted over the pushrod 76 into an annular spacing between the plate cap 58 and the piston 48 collar. The cap cover 56 may further include an outer circumferential flange which sealingly encapsulates the assembly in order to isolate the actuator assembly 102 disposed on the first side 70 against gases and fluids emanating from the patient. In this manner, removal and replacement of the diaphragm 62 is effectuated by first removing the hold down brackets 42 by loosening of the thumbscrews 44, disengaging the cap cover 56 from the plate cap 58, removing the E-ring 52 from the circumferential groove 54 of the pushrod 76 and axially sliding the cover plate 60 and diaphragm 62 off of the pushrod 76. The diaphragm 62, 0-ring 40 and cone cover 38 can then be removed or replaced prior to transferring the HFOV 10 to another patient.

As can be seen in the figures, the pushrod 76 extends axially aftwardly from the diaphragm 62 and passes through the actuator assembly 102. As was earlier mentioned, the actuator assembly 102 is generally comprised of the linear actuator 104 with the linear coil 94 being coaxially disposed thereabout. The linear actuator 104 is fixably mounted to the housing assembly 30 and is generally comprised of a shell 106 that is open on an open end 116 and closed on an opposite closed end 110. A spaced pair of axially aligned magnets 118 are disposed in annually spaced relation to the shell 106. A corresponding pair of pole pieces 120 are disposed between the pair of magnets 118 wherein such magnets 118 and pole pieces 120 are preferably disk shaped and are placed in series relative to one another. The magnet/pole piece 118, 120 assembly is secured to the closed end 110 of the linear actuator 104 which, in turn, is connected to the shell 106.

Disposed within an annular gap 68 between the shell 106 and the magnet/pole piece assembly 118, 120 is the linear coil 94 which may be generally cylindrically shaped and which comprises at least a first coil 96 disposed in axially spaced relation to a second coil 98. The linear coil 94 includes a coil carrier 112 disposed on an end opposite that from the closed end 110 of the linear actuator 104. The pushrod 76 extends through the linear actuator 104 and is securely affixed to the coil carrier 112 by means of a pushrod boss 82 which may generally disk shaped and which has a generally larger diameter than that of the pushrod 76 in order to anchor the pushrod 76 to the coil carrier 112. The coil carrier 112 may be connected to a power supply and includes windings 100 disposed about the first and second coils 96, 98 and being configured to have the appropriate polarities for operation of the actuator assembly 102.

As can be seen in FIGS. 2 and 2A, a coil clearance 108 is defined between the first and second coils 96, 98 and the shell 106. The pushrod 76 is preferably configured to rigidly support the linear coil 94 to prevent contact between the linear coil 94 and linear actuator 104. Furthermore, the pushrod 76 is preferably configured to maintain radial alignment of the linear coil 94 during reciprocation thereof with respect to the forward and aft housing 34 which comprises the housing assembly 30.

On the closed end 110 of the linear actuator 104 is a bushing housing 126 through which the pushrod 76 extends. A generally elongate pushrod 76 bushing 124 may extend axially along the length of a pushrod 76 bore 122 formed in the linear actuator 104. As was earlier mentioned, the pushrod 76 preferably extends axially through the pushrod 76 bore 122 such that the linear coil 94 is axially supported thereby.

As opposed to prior art HFOV's 10 which may utilize a plurality of angularly spaced spider springs extending radially outwardly from the pushrod 76 to the housing, the present arrangement of the HFOV 10 allows for reduced power consumption in a smaller package with the same effective clinical respiratory characteristics due to the linear coil 94 being axially supported in centered positioning by the pushrod 76 extending through the linear actuator 104. More specifically, the HFOV 10 of the present invention is specifically configured to meet the clinical requirements for supporting respiratory efforts of a patient in the range of 0.5 kg to 100 kg, preferably 30 kg and under with a maximum mean airway pressure (Paw) of less than 60 centimeters of H20 and preferably 45 centimeters of H20.

It has been shown that using an actuator assembly 102 similar to that disclosed in the Morcos reference and which is commercially available from BEI Electronics under the Model Number LA25, the HFOV 10 of the present invention has been optimized for meeting the above referenced clinical requirements. Using an actuator assembly 102 as embodied in the LA25 voice coil model wherein the linear coil 94 is suspended by the pushrod 76 bearing allows the piston 48 to oscillate at 6 Hz using approximately one-half the power required to operate an actuator assembly 102 that uses spring spiders. In addition, the HFOV 10 of the present invention is approximately three times more efficient in displacing volume against pressure than prior art HFOV's 10 utilizing spring spiders to center the linear coil 94.

A further advantage of utilizing a pushrod-mounted linear coil 94 as opposed to using spring spiders is a reduction in heat that is generated by the actuator assembly 102 during its operation. More specifically, prior art HFOV's 10 utilize voltage control in an open loop method for regulating piston 48 positioning. Piston 48 centering may be facilitated using biased voltage adjustment. Unfortunately, temperature increases in the linear coil 94 results in changes in the coil operating characteristics which effectuates piston 48 centering. The result is overshoot or undershoot of the piston 48.

Fortunately, the HFOV 10 of the present invention utilizes direct feedback in the form of a sensor such as an optical sensor 92 which is shown in FIG. 1 as being mounted on the aft housing 34 adjacent to the coil carrier 112. More specifically, FIG. 1 illustrates a rod holder 80 being fixably mounted to the coil carrier 112 and, in turn, the pushrod 76. The rod holder 80 may extend outwardly from the aft housing 34 and may be secured to a sensor rod 88 which interfaces with a sensor shaft 90 protruding outwardly from the sensor. Such a configuration provides a closed loop servo-controlled arrangement which takes advantages of direct positioning feedback in order to provide necessary adjustments in piston 48 centering. In this regard, deficiencies associated with loss of accuracy in piston 48 centering due to heat build up as suffered by the prior art HFOV's 10 is essentially overcome.

As shown in FIGS. 2 and 2A, the housing assembly 30 may include an aft housing cap 36 which is secured to the aft housing 34. An aft stop 86 may be disposed on an interior side of the aft housing cap 36 to provide a bumper against which the rod holder 80 may bear during extremes of the aft stroke of the piston 48. Likewise, a forward stop 84 may be secured to the linear actuator 104 such that the coil carrier 112 may bear there against during extreme motion of the piston 48 in the forward stroke. Preferably, the aft and forward stops 84 are fabricated of a generally resilient material in order to provide shock isolation to the actuator assembly 102.

Cooling of the actuator assembly 102 is facilitated by environmental air circulation therethrough. At a forward end 12 of the linear actuator 104 may he a set of apertures 114 formed therethrough in order to allow passage of cooling gases (i.e., air) in order to cool the linear coil 94 and linear actuator 104. Likewise, the forward housing 32 may include at least one and, preferably, several ventilation ports 78 which may be configured as semi-circular shaped slots formed in the forward housing 32. As can be seen in FIG. 2, the ventilation ports 78 provide a pathway for fluid communication of atmospheric gases into the actuator assembly 102 for convective cooling thereof.

In this manner, the need for a separate source of cooing gas and/or a cooling fan is obviated in the HFOV 10 of the present invention. The elimination of such components reduces overall power consumption while simplifying the construction of the HFOV 10. As was earlier mentioned, the use of a cooling fan in HFOV's 10 of the prior art unfortunately creates a whining noise which may be disruptive to patients in the sensitive environments within which such HFOV's 10 are typically utilized.

Referring now to FIG. 1, the HFOV 10 of the present invention is preferably supported by a suitable mounting bracket 16 which, as shown in FIGS. 1 and 2, may be comprised of a bottom plate 24 having a stand 28 affixed thereto and to which the aft housing 34 may be secured. A plurality of feet 26 may be mounted on an underside of the bottom plate 24 for non-slidably supporting the HFOV 10 on a surface. The mounting bracket 16 may further include a forward panel 18 disposed in parallel space relation to an aft panel 20 with the forward panel 18 having the forward housing 32 and cone cover 38 mounted thereto. A housing cover 22 may extend around the forward and aft panels 20 and may be secured to the bottom plate 24 for enclosing the HFOV 10.

Referring now to FIG. 3, shown is a schematic illustration of a ventilation system within which the HFOV 10 may be incorporated. As was earlier mentioned, the cone cover 38 is connected to a patient tube 146 via the opening 130 in the cone cover 38. A source of gas 144 may be connected to the patient tube 146 and through which oxygen and/or compressed air may be delivered. The patient tube 146 may be connected to the patient airways via an endotracheal tube in order to provide breathing function at the patient airway. As was earlier mentioned, vibrational energy added to the gas in the form of positive and negative airways facilitates the work of breathing by providing positive pressure within the patient airway. Such pressure has been found to enhance both inhalation and exhalation phases wherein carbon dioxide is removed from the patient's lungs.

The HFOV 10 promotes the diffusion of oxygen and carbon dioxide in a manner to enhance gas exchange. Ideally, a square pressure wave generated by the HFOV 10 has been found to effectuate maximum volume displacement at a minimum amount of pressure. Accordingly, as shown in FIG. 3, a pressure measurement may be taken at the patient airway in the HFOV 10 of the present invention. The pressure measurement may in turn be fed to a microprocessor of an outer control loop 142 system for monitoring and regulating operation of an HFOV 10 effective to generate the desired pressure profile within the patient airways during reciprocation of the piston 48. Also shown in FIG. 3 is an exhalation port 148 extending from the patient tube 146 and through which gases form the patient's lungs (i.e., C02) may be discharged out of the ventilation system. A one-way valve 150 may be included with the exhalation port 148 to eliminate entry of atmospheric air during the inspiration phase.

The operation of the HFOV 10 will now be described with reference to the figures. The source of gas 144, such as pressurized gas, is connected to the patient tube 146 and is delivered thereto at a desired flow rate (i.e., a bias flow rate). A valve 150 may be included in the line from the gas source 144 which extends to the patient tube 146. The valve 150 is preferably operative to maintain static pressure within the patient's lungs in a partially inflated condition. Gas is exhaled by the patient to the exhalation port 148 via the one-way valve 150. Oxygen within the gas is diffused into the patient's lungs aided by the negative and positive pressure waves generated by the HFOV 10.

The positive and negative pressure waves are created by the HFOV 10 as a result of the reciprocation of the piston 48 and, hence, by reciprocation of the diaphragm 62 within the housing assembly 30. Current applied to the linear coil 94 causes reciprocation (i.e., back-and-forth motion) relative to the linear actuator 104. Ideally, the inner control loop 140 as shown in FIG. 3 operates in conjunction with the optical sensor 92 to regulate and maintain the position of the pushrod 76 and, hence, the piston 48 in a neutral position. Due to the direct attachment of the piston 48 to the diaphragm 62, the piston 48 move in both forward and aft strokes in unison with the diaphragm 62 which prevents the slapping motion inherent in prior art HFOV's 10. Furthermore, the deep radius groove 64 of the diaphragm 62 in the present invention moves by a quiet rolling motion. Because the groove 64 is non-inverting, the popping sound common to prior art HFOV's 10 is not produced by the HFOV 10 of the present invention.

As was earlier mentioned, power consumption of the actuator assembly 102 is also reduced due to elimination of spring forces generated by spring spiders that were utilized for centering and suspending the linear coil 94 of the prior art HFOV's 10. In this manner, minimal frictional forces must be overcome in oscillating the piston 48. Instead, the linear coil 94 is mounted or suspended on the pushrod 76 which slides axially within the pushrod 76 bushing 124 passing centrally through the linear actuator 104.

Transfer of the HFOV 10 from one patient to the next is facilitated through the use of a removable cone cover 38 which may be removed simply by loosening the thumbscrews 44 followed by removal of the hold down brackets 42. In this manner, the diaphragm 62 may be easily replaced or disinfected and reused when transferring the apparatus between patients by simply removing the cap cover 56, E-ring 52, plate cap 58, cover plate 60 and diaphragm 62, Cooling of the actuator assembly 102 is facilitated through the use of a plurality of ventilation ports 78 formed in the forward housing 32. Air passing from the atmosphere or a specific cooling air source enters the housing assembly 30 through the ventilation ports 78 whereupon movement of the piston 48 forces the cooling air through the apertures 114 formed in the closed end 110 of the linear actuator 104. In this manner, convective cooling of the linear coil 94 and linear actuator 104 is facilitated.

Additional modifications and improvements of the present invention may also be apparent to those of ordinary skill in the art. Thus, the particular combination of parts described and illustrated herein is intended to represent only certain embodiments of the present invention and is not intended to serve as limitations of alternative devices within the spirit and scope of the present invention.

What is claimed is:
1. A high frequency oscillating ventilator, comprising:
a housing assembly;
a disk-shaped piston disposed on a pushrod and comprising a flange that extends around a peripheral edge thereof;
a disk-shaped diaphragm sealingly dividing the housing assembly into a first side and a second side and being operatively engageable to the disk-shaped piston, the disk-shaped diaphragm having a rolling portion that (i) is configured to roll along a side portion of the disk-shaped piston responsive to movement of the disk-shaped piston and (ii) comprises a deep radius groove formed about a periphery thereof;
wherein the housing assembly includes a cylinder bore disposed on the first side;

wherein the cylinder bore and the flange of the disk-shaped piston are separated by an annular gap, and the deep radius groove is disposed in the annular gap; and wherein the pushrod extends through the disk-shaped piston and the disk-shaped diaphragm.

2. The high frequency oscillating ventilator of claim 1, further comprising:
a linear coil having the pushrod extending axially therethrough; and
a linear actuator having a push rod bore formed axially therethrough that is sized and configured to axially slidably receive the pushrod.

3. The high frequency oscillating ventilator of claim 1, wherein the disk-shaped piston is mounted at a first end of the pushrod, the high frequency oscillating ventilator further comprising a linear coil mounted on a second opposite end of the pushrod.

4. The high frequency oscillating ventilator of claim 1, further comprising a disk-shaped cover plate having a lip formed about a peripheral edge thereof wherein the lip is formed complementary to the flange such that the disk-shaped diaphragm is captured in a manner that limits flexing of the disk-shaped diaphragm to the deep radius groove.

5. The high frequency oscillating ventilator of claim 1, wherein the deep radius groove is configured to be non-inverting during reciprocation of the disk-shaped piston.

6. The high frequency oscillating ventilator of claim 1, wherein the disk-shaped diaphragm is replaceable and directly affixed to the disk-shaped piston during reciprocation thereof.

7. The high frequency oscillating ventilator of claim 1, further comprising an opening formed on the second side configured to be fluidly connected to a patient's airway for delivering gas thereto, wherein reciprocation of the disk-shaped diaphragm is configured to alternately produce positive and negative pressure waves in the gas in the patient's airway, and wherein the housing assembly includes at least one ventilation port formed in the first side.

8. The high frequency oscillating ventilator of claim 7, further comprising a linear actuator and a linear coil, wherein the linear actuator includes at least one aperture formed therethrough for ventilating the linear coil.

9. A high frequency oscillating ventilator, comprising:
a disk-shaped piston comprising a flange that extends around a peripheral edge thereof;
a disk-shaped cover plate;
a disk-shaped diaphragm affixed directly to the disk-shaped piston and comprising a deep radius groove formed about a periphery thereof, the disk-shaped diaphragm being captured between the disk-shaped piston and the disk-shaped cover plate;
wherein the deep radius groove of the disk-shaped diaphragm (i) is disposed in an annular gap between the flange of the disk-shaped piston and a cylinder bore of a housing assembly of the high frequency oscillating ventilator, and (ii) forms a rolling portion configured to roll along the flange of the disk-shaped piston as the disk-shaped piston moves.

10. The high frequency oscillating ventilator of claim 9, further comprising:
the housing assembly; and
a pushrod that extends through the disk-shaped piston, the disk-shaped diaphragm, and the disk-shaped cover plate.

11. The high frequency oscillating ventilator of claim 10, wherein the disk-shaped cover plate comprises a lip formed about a peripheral edge thereof and wherein the lip is formed complementary to the flange of the disk-shaped piston such that the disk-shaped diaphragm is captured in a manner that limits flexing of the disk-shaped diaphragm to the deep radius groove.

12. The high frequency oscillating ventilator of claim 10, wherein:
the disk-shaped diaphragm sealingly divides the housing assembly into first and second sides;
the housing assembly includes a cone cover; and
the disk-shaped diaphragm and cone cover collectively enclose the second side.

13. The high frequency oscillating ventilator of claim 12, wherein the cone cover is configured to be removably attached to the housing assembly.

14. The high frequency oscillating ventilator of claim 12, wherein the housing assembly includes at least one ventilation port formed in the first side for cooling the actuator assembly, wherein the housing assembly includes an opening formed on the second side and being fluidly connected to a patient's airway for delivering gas thereto, and wherein an actuator assembly is configured to effectuate reciprocation of the disk-shaped piston and the disk-shaped diaphragm to alternately produce positive and negative pressure waves in the gas in the patient's airway.

15. A method, comprising:
alternately producing positive and negative pressure waves in a gas in a patient's airway via an opening in a housing assembly of a high frequency oscillating ventilator, the opening fluidly connected to the patient's airway, wherein alternately producing the positive and negative pressure waves comprises reciprocating a disk-shaped diaphragm disposed within the housing assembly, and wherein:
the high frequency oscillating ventilator comprises a disk-shaped piston disposed on a pushrod and having a flange that extends around a peripheral edge thereof;
the disk-shaped diaphragm sealingly divides the housing assembly into a first side and a second side and is reciprocated by the disk-shaped piston, the disk-shaped diaphragm having a rolling portion that (i) rolls along a side portion of the disk-shaped piston during reciprocation and (ii) comprises a deep radius groove formed about a periphery thereof;
the housing assembly includes a cylinder bore disposed on the first side;
the cylinder bore and the flange of the disk-shaped piston are separated by an annular gap, and the deep radius groove is disposed in the annular gap;
the opening is formed on the second side; and
the pushrod extends through the disk-shaped piston and the disk-shaped diaphragm.

16. The method of claim 15, wherein the deep radius groove is sized and configured complementary to the cylinder bore.

17. The method of claim 16, wherein the high frequency oscillating ventilator further comprises a cover plate having a lip formed about a peripheral edge thereof and wherein the lip is formed complementary to the flange such that the disk-shaped diaphragm is captured in a manner that limits flexing of the disk-shaped diaphragm to the deep radius groove.

18. The method of claim 15, wherein:
the housing assembly includes a cone cover; and
the disk-shaped diaphragm and cone cover collectively enclose the second side.

19. The method of claim 18, wherein the cone cover is configured to be removably attached to the housing assembly.

20. The method of claim 15, further comprising cooling an actuator assembly of the high frequency oscillating ventilator using at least one ventilation port formed in the first side of the housing assembly.

\* \* \* \* \*